United States Patent [19]

Ikimi et al.

[11] Patent Number: 6,120,653
[45] Date of Patent: Sep. 19, 2000

[54] SEPARATION AND PURIFICATION METHOD OF T-BUTYL-METHYLPHENOL ISOMER

[75] Inventors: Kiyoshi Ikimi; Susumu Tsukada, both of Oita; Masaaki Toma, Kashihara, all of Japan

[73] Assignee: Sumitomo Chemical Company, Limited, Okaka-fu, Japan

[21] Appl. No.: 09/076,806

[22] Filed: May 13, 1998

[30] Foreign Application Priority Data

May 13, 1997 [JP] Japan ................................. 9-122243

[51] Int. Cl.[7] .......................... B01D 3/00; C07C 27/28; C07C 37/74
[52] U.S. Cl. .................... 203/74; 203/81; 568/749; 568/750; 568/913
[58] Field of Search .................. 203/71, 73, 74, 203/81; 568/756, 749, 750–751, 784, 913

[56] References Cited

U.S. PATENT DOCUMENTS

| | | | |
|---|---|---|---|
| 4,046,818 | 9/1977 | Leston | 568/913 |
| 4,325,789 | 4/1982 | Wust et al. | 203/70 |
| 4,415,409 | 11/1983 | Zndkevitch et al. | 568/913 |
| 4,423,253 | 12/1983 | Leston | 568/756 |
| 5,262,016 | 11/1993 | Lorenzoni et al. | 203/74 |
| 5,264,085 | 11/1993 | Inaba et al. | 568/918 |

FOREIGN PATENT DOCUMENTS

4324673A1  1/1994  Germany .

*Primary Examiner*—Virginia Manoharan
*Attorney, Agent, or Firm*—Birch, Stewart, Kolasch & Birch LLP

[57] ABSTRACT

A method is provided for industrially advantageously and effectively separating 4M2B and 3M6B from a t-butylcresol mixture containing 2-t-butyl-4-methylphenol (4M2B), 2-tbutyl-5-methylphenol (3M6B), compounds having a lower boiling point than that of 4M2B and compounds having a higher boiling point than that of 3M6B derived from a m,p-cresol mixture.

7 Claims, No Drawings

SEPARATION AND PURIFICATION METHOD OF T-BUTYL-METHYLPHENOL ISOMER

BACKGROUND OF THE INVENTION

1. Field of the Invention

The present invention relates to a method for separating and purifying 2-t-butyl-4-methylphenol and 2-t-butyl-5-methylphenol from a t-butylcresol mixture.

2. Prior Art 2-t-butyl-4-methylphenol (4M2B) and 2-t-butyl-5-methylphenol (3M6B) are known as important compounds in the filed of agricultural chemicals and the like and are widely used.

For obtaining 4M2B or 3M6B, there is a known method in which m-cresol and p-cresol are previously separated from a m,p-cresol mixture which is industrially easily available, and each isomer is butylated.

Also, a method is known in which a m,p-cresol mixture is dibutylated to obtain a mixture of 2,6-di-t-butyl-4-methylphenol (4M26B) and 4,6-di-t-butyl-3-methylphenol (3M46B), the mixture is separated, then, each isomer is de-monobutylated or transalkylated with cresols.

However, in the former method, m-cresol and p-cresol must be previously separated from a m,p-cresol mixture, and further, after the separated isomers are respectively butylated, 4M2B or 3M6B must be separated and purified again by distillation and the like from the reaction product containing unreacted cresol and a dibutylated by-product compound.

Additionally in the latter method, 4M26B and 3M46B must be previously separated from the dibutylated reaction mixture of a m,p-cresol mixture, and further, after the isomers are respectively de-monobutylated or transalkylated with cresols, 4M2B or 3M6B must be separated and purified again by distillation and the like from the reaction product containing cresols and an unreacted dibutylated compound.

As described above, for obtaining 4M2B and 3M6B in the conventional methods, separation into a m-isomer system and a p-isomer system such as separation into m-cresol and p-cresol in raw materials for butylation reaction of a m,p-cresol mixture or separation into a dibutyl isomer derived from m-cresol and a dibutyl isomer derived from p-cresol after dibutylation reaction has been required.

The reason for this is that it has been supposed to be difficult to separate and purify 4M2B and 3M6B by distillation from such a t-butylcresol mixture since the difference in boiling points of 4M2B and 3M6B (127° C. and 132° C. respectively, each measured at 2.67 KPa) is small, and a de-monobutylated or transalkylated reaction mixture with cresols of a dibutylated reaction mixture of a m,p-cresol mixture or a butylated reaction mixture of a m,p-cresol mixture contains compounds having a lower boiling point than that of 4M2B and compounds having a higher boiling point than that of 3M6B (Industrial and Engineering Chemistry, 35, No. 3, 264 (1943)).

It is industrially advantageous from the viewpoint of operation to separate 4M2B and 3M6B from a t-butylcresol mixture containing 3M6B, 4M2B, compounds having a higher boiling point than that of 3M6B and compounds having a lower boiling point than that of 4M2B obtained by using an industrially easily available m,p-cresol mixture as a raw material without any treatment, and without separation into a m-isomer system and a p-isomer system in its raw material stage, therefore, development of a method for such a separation has been strongly desired.

SUMMARY OF THE INVENTION

Under these circumstances, the present inventors have studied a method to effectively separate 4M2B and 3M6B from a t-butylcresol mixture comprising, as a component, 2-t-butyl-4-methylphenol (4M2B), 2-t-butyl-5-methylphenol (3M6B), compounds having a lower boiling point than that of 4M2B and compounds having a higher boiling point than that of 3M6B derived from a m,p-cresol mixture in an industrially advantageous manner, and as a result, attaining the present invention.

The present invention provides a method for separation and purification of a t-butyl-methylphenol isomer from a t-butylcresol mixture comprising, as a component, 2-t-butyl-4-methylphenol (4M2B), 2-t-butyl-5methylphenol (3M6B), compounds having a lower boiling point than that of 4M2B and compounds having a higher boiling point than that of 3M6B, which comprises at least three times distillation operations wherein each distillation operation comprises separating at least one component having a lower boiling point and at least one component having a higher boiling point from the mixture or components resulted in the prior distillation operation.

DETAILED DESCRIPTION OF THE PREFERRED EMBODIMENTS

The t-butylcresol mixture to be used in the present invention comprises, as a component, 2-t-butyl-4-methylphenol (4M2B), 2-t-butyl-5-methylphenol (3M6B), compounds having a lower boiling point than that of 4M2B and compounds having a higher boiling point than that of 3M6B, all of which has derived from m- or p-cresols.

Such a t-butylcresol mixture is known, and examples thereof include a reaction mixture obtained by butylation reaction of a m,p-cresol mixture, a reaction mixture obtained by transalkylation of cresols with di-t-butylcresols which are dibutylated compounds of m- and p-cresols, and a reaction mixture obtained by de-monobutylation reaction of the same di-t-butylcresols as described above.

The m,p-cresol mixture used for the butylation reaction of a m,p-cresol mixture is a mixture of a meta isomer and a para isomer, and the mixture may contain technically admissible amount of an ortho isomer.

As the butylation agent, isobutylene is usually used, and an isobutylene gas mixture containing other butene gases such as 1-butene and/or 2-butene also may be used, because the latter butene gases are far less reactive than isobutylene and do not form any substantial amount of impurities.

In such a butylation reaction, reaction conditions for producing a monobutylated isomer in large amount are selected, however, formation of a dibutylated isomer is inevitable, and the reaction product contains compounds having a lower boiling point than that of 4M2B such as unreacted cresol and compounds having a higher boiling point than that of 3M6B such as a dibutylated isomer together with intended 4M2B and 3M6B.

The proportion of cresol to di-t-butylcresol in the transalkylation reaction of cresols with di-t-butylcresols which are dibutylated compounds of m- and p-cresols are not particularly restricted, and the reaction is usually conducted with the proportion around 1:1 in view of reaction efficiency.

Also, in such a transalkylation reaction, the reaction product contains compounds having a lower boiling point than that of 4M2B such as unreacted cresol, and compounds having higher boiling point than that of 3M6B such as dibutylated cresols together with the desired products, 4M2B and 3M6B in as the above-described case.

Further, also in the de-monobutylation reaction of di-t-butylcresol, both butyl groups leave to form cresol and an unreacted di-t-butylcresols remains together with the formed 4M2B and 3M6B.

The catalyst used for a usual aromatic-alkylation reaction and a de-alkylation reaction may also be advantageously used in such a butylation reaction of a m,p-cresol mixture, transalkylation of cresols with di-t-butylcresols, and de-monobutylation reaction of di-t-butylcresols.

The catalyst usually includes an acid catalyst, and examples thereof include protonic acids such as sulfuric acid and the like, Lewis acids such as aluminum chloride and the like, and solid acids such as a hetero-polyacid and the like.

Although such a t-butylcresol mixture as described above and the like wherein the composition of the mixture is not specifically limited may be used in the separation and in the purification of the present invention without any treatment, it is usually washed with an alkali, then, used for distillation and purification. The alkali used is not particularly restricted, and an aqueous sodium hydroxide solution which is industrially easily available and easily handled is preferred.

For separating and purifying 2-t-butyl-4-methylphenol (4M2B) or 2-t-butyl-5-methylphenol (3M6B) from such a t-butylcresol mixture, at least three times distillation operations wherein each distillation operation comprises separating at least one component having a lower boiling point and at least one component having a higher boiling point from the mixture or components resulted in the prior distillation operation.

The distillation operation for separating at least one component having a lower boiling point and at least one component having a higher boiling point can be optionally selected and combined. Typical examples thereof include the following methods.

(1) A method comprises distillation operations of:
(i) separating 4M2B cut containing compounds having a lower boiling point than that of 4M2B and a 3M6B cut containing compounds having a higher boiling point than that of 3M6B from the t-butylcresol mixture,
(ii) separating 4M2B from the 4M2B cut, and
(iii) separating 3M6B from the 3M6B cut, wherein the order of (ii) and (iii) is optionally set, and (ii) and (iii) may be effected simultaneously.

(2) A method comprises distillation operations of:
(i) separating compounds having a higher boiling point than that of 3M6B from the t-butylcresol mixture to obtain a cut containing the remaining components,
(ii) separating compounds having a lower boiling point than that of 4M2B from the cut to obtain a cut containing 4M2B and 3M6B, and
(iii) separating 4M2B and 3M6B from the cut.

(3) A method comprises distillation operations of:
(i) separating compounds having a lower boiling point than that of 4M2B from the t-butylcresol mixture to obtain a cut containing the remaining components,
(ii) separating compounds having a higher boiling point than that of 3M6B from the cut to obtain a cut containing 4M2B and 3M6B, and
(iii) separating 4M2B and 3M6B from the cut.

(4) A method comprises distillation operations of:
(i) separating compounds having a higher boiling point than that of 3M6B from the t-butylcresol mixture to obtain a cut containing the remaining components,
(ii) separating 3M6B from the cut, and
(iii) separating 4M2B.

(5) A method comprises distillation operations of:
(i) separating compounds having a lower boiling point than that of 4M2B from the t-butylcresol mixture to obtain a cut containing 4M2B, 3M6B and compounds having a higher boiling point than that of 3M6B,
(ii) separating 4M2B from the cut, and
(iii) separating 3M6B.

The distillation operation can be conducted under atmospheric pressure and reduced pressure. However, since distillation temperature is high under atmospheric pressure, it is industrially preferable that the distillation temperature such as bottom temperature is 200° C. or lower under reduced pressure in view of product quality, operability, utility and the like. Therefore, it is preferable that the operation pressure is usually 32 Kpa or less, preferably from 1.5 to 30 Kpa.

The distillation operation for separating these lower boiling point and higher boiling point components may be conducted with simple-distillation, however, a multistage distillation column is usually used. The theoretical stage number is optionally selected depending on raw material composition, and for obtaining a product having high purity, a higher theoretical stage number is more preferable, and particularly, in distillation operation for separating 4M2B and 3M6B, it is preferable that the theoretical stage number is from 30 to 100, more specifically from 60 to 80. Of course, a higher theoretical stage number can be used, however, in this case, desired pressure sometimes can not be maintained due to pressure loss, and a large scale apparatus is necessary.

The type of distillation column is not specifically limited, and examples thereof include those having a tray stage, a packing and the like, and examples of the packing include Pall® ring, Sulzer® Wire Gauge BX packing and the like (Distillation Design, by H. Z. Kister).

EXAMPLE

The following examples further illustrate the present invention but do not limit the scope thereof.

Example 1

Abbreviation

4M2B: 2-t-butyl-4-methylphenol

3M6B: 2-t-butyl-5-methylphenol dibutylated isomers: a mixture of 2,6-di-t-butyl4-methylphenol and 4,6-di-t-butyl-3-methylphenol Into a reaction vessel equipped with a stirrer, gas blowing tube, thermometer and condenser is fed cresol into which sulfuric acid has been dissolved (sulfuric acid is dissolved in 1.2% by weight based on 100% by weight of cresol) at 795 g/hr, further, butylation reaction is conducted for 8 hours at 65° C. under normal pressure with blowing in an isobutyrene mixed gas containing 1-butene, 2-butene and the like, and the resulted butylated reaction mixture is neutralized with an aqueous NaOH solution. For the neutralization, 1.5 equivalent NaOH is added per charged sulfuric acid and the treatment is conducted for 3 hours at 110° C., then an aqueous layer is separated, and the resulted oil layer is washed with water to obtain 11.79 kg of t-butylcresol mixture (cresolcontent6.4%, 4M2B contentl6.3%, 3M6B content 13.3%, dibutylated isomer content 58.6%, content of other components 5.4%).

The product is rectified using a rectification column having a theoretical stage number of 80 at a feed stage number of 53, a reflux ratio of 20, a column top pressure of 6.7 kPa, and a column top temperature of 127.6° C., to obtain a distillate containing 27.6% of cresol, 70.0% of 4M2B and 0.3% of 3M6B and a bottom extract containing 0.1% of 4M2B, 17.2% of 3M6B and 76.4% of a dibutylated isomer. The bottom pressure in this operation is 10.7 kPa, and the bottom temperature is 180.1° C.

This distillate is rectified using a rectification column having a theoretical stage number of 22 at a feed stage number of 11, a reflux ratio of 3, a column top pressure of 13.3 kPa, and a column top temperature of 127.1° C., to obtain a distillate containing 93.2% of cresol and a bottom extract containing 99.1% of 4M2B and 0.5% of 3M6B. The bottom pressure in this operation is 14.7 kPa, and bottom temperature is 168.7° C.

The bottom extract obtained in the first rectification is rectified using a rectification column having a theoretical stage number of 30 at a feed stage number of 14, a reflux ratio of 6, a column top pressure of 4.0 kPa, and a column top temperature of 138.5° C., to obtain a distillate containing 0.6% of 4M2B and 99.1% of 3M6B and a bottom extract containing 0.2% of 3M6B and 92.2% of dibutylated isomers. The bottom pressure in this operation was 4.8 kPa, and the bottom temperature is 164.5° C.

Example 2

The t-butylcresol mixture obtained in Example 1 (cresol content 6.4%, 4M2B content 16.3%, 3M6B content 13.3%, dibutylated isomer content 58.6%, content of other components 5.4%) is rectified using a rectification column having a theoretical stage number of 30 at a feed stage number of 14, a reflux ratio of 6, a column top pressure of 4.0 kPa, and a column top temperature of 121.3° C., to obtain a distillate containing 17.5% of cresol, 44.7% of 4M2B and 36.4% of 3M6B and a bottom extract containing 92.3% of a dibutylated isomer. The bottom pressure in this operation is 4.8 kPa, and the bottom temperature is 164.6° C.

This distillate is rectified using a rectification column having a theoretical stage number of 22 at a feed stage number of 11, a reflux ratio of 3, a column top pressure of 4.0 kPa, and a column top temperature of 100.7° C., to obtain a distillate containing 93.3% of cresol and a bottom extract containing 0.1% of cresol, 55.0% of 4M2B and 44.7% of 3M6B. The bottom pressure in this operation is 5.3 kPa, and the bottom temperature is 143.1° C.

The bottom extract is rectified using a rectification column having a theoretical stage number of 80 at a feed stage number of 53, a reflux ratio of 30, a column top pressure of 13.3 kPa, and a column top temperature of 166.0° C., to obtain a distillate containing 99.1% of 4M2B and 0.5% of 3M6B and a bottom extract containing 0.7% of 4M2B and 99.3% of 3M6B. The bottom pressure in this operation is 17.3 kPa, and the bottom temperature is 178.9° C.

Example 3

The t-butylcresol mixture obtained in Example 1 (cresol content 6.4 %, 4M2B content 16.3 %, 3M6B content 13.3 %, dibutylated isomer content 58.6%, content of other components 5.4%) is rectified using a rectification column having a theoretical stage number of 22 at a feed stage number of 11, a reflux ratio of 3, a column top pressure of 13.3 kPa, and a column top temperature of 127.1° C., to obtain a distillate containing 93.3% of cresol and a bottom extract containing 17.5% of 4M2B, 14.3% of 3M6B and 62.9% of a dibutylated isomer. The bottom pressure in this operation is 14.7 kPa, and the bottom temperature is 183.3° C.

This bottom extract is rectified using a rectification column having a theoretical stage number of 80 at a feed stage number of 53, a reflux ratio of 35, a column top pressure of 6.7 kPa, and a column top temperature of 147.0° C., to obtain a distillate containing 99.1% of 4M2B and 0.5% of 3M6B and a bottom extract containing 17.2% of 3M6B and 76.4% of a dibutylated isomers. The bottom pressure in this operation is 10.7 kPa, and the bottom temperature is 180.1° C.

Further, this bottom extract is rectified using a rectification column having a theoretical stage number of 30 at a feed stage number of 14, a reflux ratio of 8, a column top pressure of 4.0 kPa, and a column top temperature of 138.5° C., to obtain a distillate containing 0.7% of 4M2B and 99.3% of 3M6B and a bottom extract containing 0.2% of 3M6B and 92.2% of dibutylated isomers. The bottom pressure in this operation is 4.8 kPa, and the bottom temperature is 164.5° C.

According to the method of the present invention, 4M2B and 3M6B can be industrially advantageously and efficiently separated from a t-butylcresol mixture derived from a m,p-cresol mixture.

What is claimed is:

1. A method for separation and purification of a t-butyl-methylphenol isomer, selected from the group consisting of 2-t-butyl-4-methylphenol and 2-t-butyl-5-methylphenol, from a t-butylcresol mixture comprising:

(a) 2-t-butyl-4-methylphenol;

(b) 2-t-butyl-5-methylphenol;

(c) compounds having a lower boiling point than that of 2-t-butyl-4-methylphenol; and (d) compounds having a higher boiling point than that of 2-t-butyl-5-methylphenol;

which method comprises:

a)
  i) distilling said t-butylcresol mixture to obtain a distillate comprising:
    2-t-butyl-4-methylphenol and compounds having a lower boiling point than that of 2-t-butyl-4-methylphenol, and
  a bottom product comprising:
    2-t-butyl-5-methylphenol and compounds having a higher boiling point than that of 2-t-butyl-5-methylphenol;
  ii) distilling the distillate obtained in step a) i) to obtain 2-tbutyl-4-methylphenol as a bottom product; and
  iii) distilling the bottom product obtained in step a) i) to obtain 2-t-butyl-5-methylphenol as a distillate; or b)
  i) distilling said t-butylcresol mixture to obtain a bottom product comprising:
    compounds having a higher boiling point than that of 2-t-butyl-5-methylphenol; and
  a distillate comprising:
    compounds having a lower boiling point than that of 2-t-butyl-4-methylphenol;
    2-t-butyl-4-methylphenol and 2-t-butyl-5-methylphenol;
  ii) distilling the distillate obtained in step b) i) to obtain a bottom product comprising:
    2-t-butyl-4-methylphenol and 2-t-butyl-5-methylphenol; and
  iii) distilling the bottom product obtained in step b) ii) to obtain 2-t-butyl-4-methylphenol as a distillate and 2-t-butyl-5-methylphenol as a bottom product; or c)
  i) distilling said t-butylcresol mixture to obtain a bottom product comprising:

compounds having a higher boiling point than that of 2-t-butyl-5-methylphenol, 2-t-butyl-4-methylphenol and 2-t-butyl-5-methylphenol; and a distillate comprising:
compounds having a lower boiling point than that of 2-t-butyl-4-methylphenol;

ii) distilling the bottom product obtained in step c) i) to obtain a distillate comprising:
2-t-butyl-4-methylphenol and 2-t-butyl-5-methylphenol; and iii) distilling the distillate obtained in step c) ii) to obtain 2-t-butyl-4-methylphenol as a distillate and 2-t-butyl-5-methylphenol as a bottom product; or d)
i) distilling said t-butylcresol mixture to obtain a bottom product comprising:
compounds having a higher boiling point than that of 2-t-butyl-5-methylphenol; and a distillate comprising:
compounds having a lower boiling point than that of 2-t-butyl-4-methylphenol, 2-t-butyl-4-methylphenol and 2-t-butyl-5-methylphenol;

ii) distilling the distillate obtained in step d) i) to obtain 2-t-butyl-5-methylphenol as a bottom product, and a distillate comprising:
compounds having a lower boiling point than that of 2-t-butyl-4-methylphenol and 2-t-butyl-4-methylphenol; and iii) distilling the distillate obtained in step d) ii) to obtain 2-t-butyl-4-methylphenol as a bottom product; or e)
i) distilling said t-butylcresol mixture to obtain a bottom product comprising compounds having a higher boiling point than that of 2-t-butyl-5-methylphenol, 2-t-butyl-4-methylphenol and 2-t-butyl-5-methylphenol; and a distillate comprising:
compounds having a lower boiling point than that of 2-t-butyl-4-methylphenol;

ii) distilling the bottom product obtained in step e) i) to obtain:
2-t-butyl-4-methylphenol as a distillate; and
a bottom product comprising 2-t-butyl-5-methylphenol and compounds having a higher boiling point than that of 2-t-butyl-5-methylphenol; and iii) distilling the bottom product obtained in step e) ii) to obtain 2-t-butyl-5-methylphenol as a distillate.

2. The method according to claim 1, wherein the t-butylcresol mixture is a reaction mixture obtained by butylation reaction of a m,p-cresol mixture.

3. The method according to claim 1, wherein the t-butylcresol mixture is a reaction mixture obtained by transalkylation of cresols with di-t-butylcresols.

4. The method according to claim 1, wherein the t-butylcresol mixture is a reaction mixture obtained by de-butylation reaction of di-t-butylcresols.

5. The method according to claim 1, wherein each distillation occurs at a distillation temperature of 200° C. or lower.

6. The method according to claim 1, wherein a rectification column having a theoretical stage number of 30 to 100 is used in the distillation operation for separating 2-t-butyl-4-methylphenol and 2-t-butyl-5-methylphenol.

7. The method according to claim 1, wherein said compounds having a lower boiling point than that of 2-t-butyl-4-methylphenol and said compounds having a higher boiling point than that of 2-t-butyl-5-methylphenol comprise m-cresol and p-cresol.

* * * * *